United States Patent [19]

Shoesmith, deceased

[11] Patent Number: Plant 6,155

[45] Date of Patent: Apr. 19, 1988

[54] CHRYSANTHEMUM PLANT NAMED CASTANET

[75] Inventor: Leonard H. Shoesmith, deceased, late of Woking Surrey, England, by May V. Shoesmith, executrix

[73] Assignee: Ball PanAm Plant Company, Parrish, Fla.

[21] Appl. No.: 872,910

[22] Filed: Jun. 11, 1986

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Castanet having bright clear yellow ray florets which are relatively long and slightly reflexed at the tips, strong stems with long peduncles, good production, nine week response, capitulum up to 100 mm in diameter, and good shipping and keeping qualities.

1 Drawing Sheet

The present invention comprises a new and distinct cultivar of *Chrysanthemum morifolium,* Ramat., hereinafter referred to by the cultivar name Castanet.

Castanet is a product of a planned breeding program which had the objective of creating new Chrysanthemum cultivars having improved characteristics when compared with the well-known Marble family of daisy type sprays.

Castanet was originated from a hybridization made in a controlled breeding program in Westfield, Woking, England in 1977. The male and female parents are unknown at this time.

Castanet was discovered and selected as one flowering plant within the progeny of the stated parentage by Leonard H. Shoesmith in November of 1978 in a controlled environment in West Chicago, Ill., and was given the code #SP-78-1173-YS.

The first act of asexual reproduction of Castanet was accomplished when vegetative cuttings were taken from the initial selection in February of 1979 in a controlled environment in West Chicago, Ill. by a technician working under formulations established and supervised by Leonard H. Shoesmith. Horticultural examination of selected units initiated in May of 1979 has demonstrated that the combination of characteristics as herein disclosed for Castanet are firmly fixed and are retained through successive generations of asexual reproduction.

Castanet has not been observed under all possible environmental conditions. The phenotype may vary significantly with variations in environment such as temperature, light intensity and day length. The following observations, measurements and comparisons describe plants grown in Parrish, Fla. under greenhouse conditions which approximate those generally used in commercial practice.

The following traits have been repeatedly observed and are determined to be basic characteristics of Castanet, which in combination distinguish this Chrysanthemum as a new and distinct cultivar.

(1) Nine week response.

(2) Strong stems with long peduncles; up to 70 cm long.

(3) Good production per stem; up to 8 good useable flowers per stem.

(4) Bright, clear yellow ray florets; about 30 ray florets per capitulum.

(5) Ray florets are held upright, ends are slightly reflexed; ray florets are long, up to 45 mm, flat, elliptical with smooth margins; tip is acuminate.

(6) Bright lime green disc florets.

(7) Capitulum up to 100 mm in diameter.

(8) Ships and keeps well.

Of the many commercial cultivars know to the present inventor, the most similar in comparison to Castanet is Florida Marble. In comparison to Florida Marble, Castanet has stronger stems and more flowers per stem, stronger foliage, a brighter yellow ray floret color, better keeping, and more green disc florets. The generally flat flower form, yellow category, and daisy flower type are similar to those same characteristics of Florida Marble.

The accompanying photographic drawing shows typical inflorescence characteristics of Castanet, with colors being as nearly true as possible with illustrations of this type.

Sheet 1 is a black and white photograph, with one flower being colored to illustrate the ray and disc floret color of Castanet.

In the following description, color references are made to The Royal Horticultural Society Colour Chart. The color values were determined between Noon and 1:00 p.m. on May 29, 1986 under fluorescent light conditions at Bradenton, Fla.

Classification:

*Botanical.*—*Chrysanthemum morifolium,* Ramat., cv Castanet.

*Commercial.*—Daisy pompon or cut daisy spray.

INFLORESCENCE

A. Capitulum:

*Form.*—Flat, with ends reflexed.

*Type.*—Single.

*Diameter across face.*—Approximately 100 mm.

B. Corolla of ray florets:

*Color (general tonality from a distance of three meters).*—Bright yellow.

*Color (upper surface).*—3A.

*Color (under surface).*—3C.

C. Corolla of disc florets:

*Color* (*mature*).—Yellow.
*Color* (*immature*).—Lime green.

D. Reproductive organs:
*Androecium.*—Present in disc florets only; many.
*Gynoecium.*—Present in ray and disc florets; many.

PLANT

A. General appearance:
*Height.*—1-2 meters at finish.

B. Foliage:
*Color* (*upper surface*).—147A.
*Color* (*under surface*).—147B.

*Shape.*—Deeply lobed and slightly serrated.

I claim:

1. A new and distinct cultivar of Chrysanthemum plant named Castanet, as illustrated and described, and particularly characterized by its bright clear yellow ray florets which are relatively long and slightly reflexed at the tips, strong stems with long peduncles, good production, nine week response, capitulum up to 100 mm in diameter, and by its good shipping and keeping qualities.

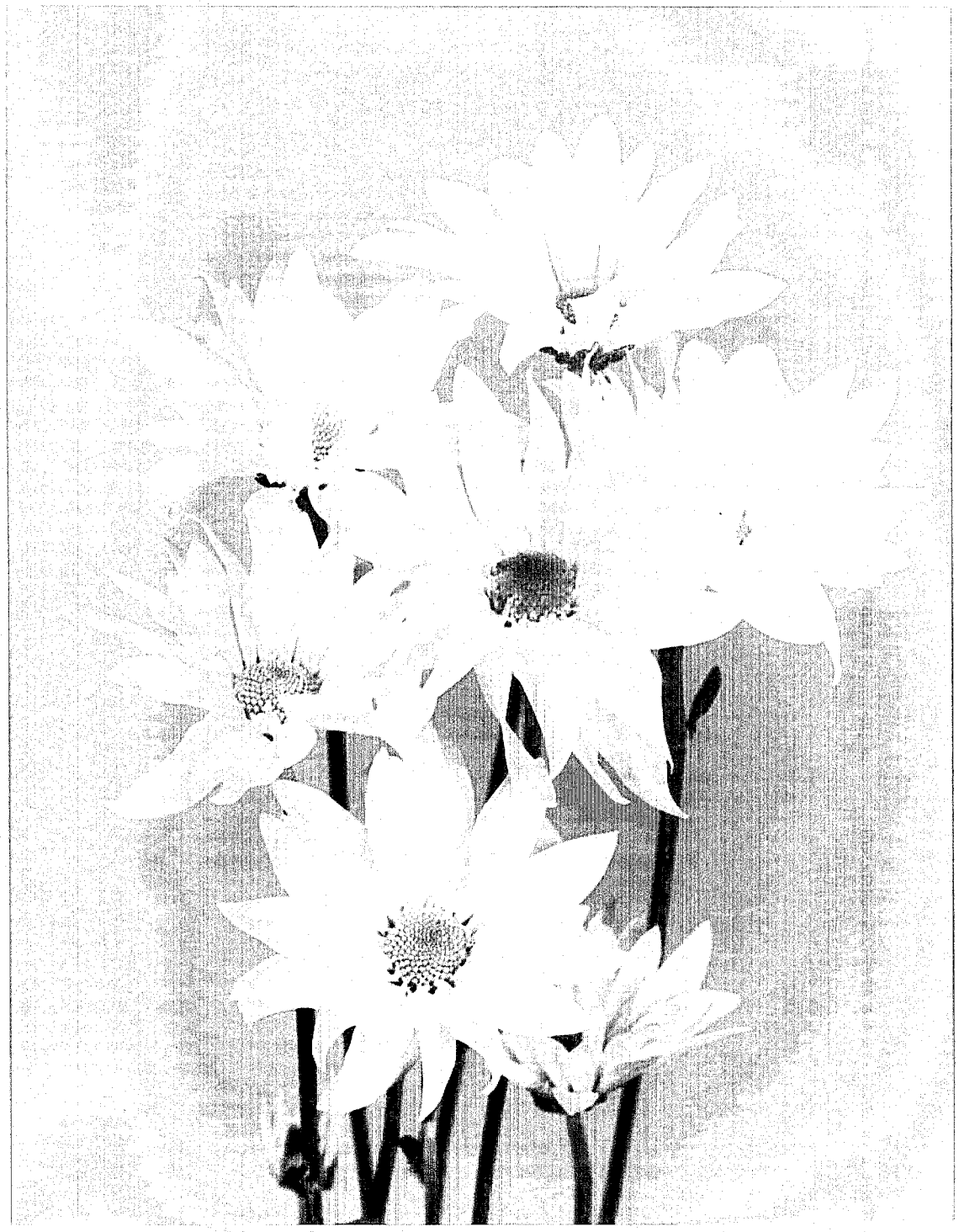

* * * * *